(12) United States Patent
Forbes et al.

(10) Patent No.: US 11,298,255 B2
(45) Date of Patent: Apr. 12, 2022

(54) ORTHOPEDIC DEVICE

(71) Applicant: OSSUR HF, Reykjavik (IS)

(72) Inventors: James Forbes, Foothill Ranch, CA (US); Stacy Wyatt, Foothill Ranch, CA (US); Yessenia Lopez, Foothill Ranch, CA (US); Irving Hu, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 68 days.

(21) Appl. No.: 16/280,254

(22) Filed: Feb. 20, 2019

(65) Prior Publication Data

US 2019/0175377 A1    Jun. 13, 2019

Related U.S. Application Data

(63) Continuation of application No. 13/331,389, filed on Dec. 20, 2011, now Pat. No. 10,231,860.

(60) Provisional application No. 61/487,478, filed on May 18, 2011, provisional application No. 61/426,188, filed on Dec. 22, 2010.

(51) Int. Cl.
    *A61F 5/01* (2006.01)
(52) U.S. Cl.
    CPC .................. *A61F 5/0109* (2013.01)
(58) Field of Classification Search
    CPC ............ A61F 5/01–0109; A61F 5/0123; A61F 5/0125; A61F 2005/0132–0179; A61F 13/06–062; A41D 13/05; A41D 13/0543; A41D 13/06; A41D 13/065; A63B 71/08; A63B 71/12; A63B 71/1225; A63B 2071/125
    See application file for complete search history.

(56) References Cited

U.S. PATENT DOCUMENTS

| | | |
|---|---|---|
| 663,749 A | 12/1900 | Gorse |
| 940,585 A | 11/1909 | Drennan |
| 2,188,718 A | 1/1940 | Jung |
| 2,524,326 A | 10/1950 | Murphy |
| 3,046,981 A | 7/1962 | Biggs, Jr. et al. |
| 3,084,685 A | 4/1963 | Lewis |
| 3,406,406 A | 10/1968 | Lutz |
| 3,786,804 A * | 1/1974 | Lewis ............... A61F 5/0125 602/16 |
| 3,789,842 A | 2/1974 | Froimson |

(Continued)

FOREIGN PATENT DOCUMENTS

| | | |
|---|---|---|
| CA | 2038948 A1 | 2/1991 |
| DE | 3028381 A1 | 2/1982 |

(Continued)

OTHER PUBLICATIONS

Ossur Orthopedics Catalog 2009, pp. 1, 41-47 and 100.
Partial Search Report issued in PCT/US2011/065749, dated Apr. 2, 2012, 2 pages.

*Primary Examiner* — Michelle J Lee
(74) *Attorney, Agent, or Firm* — Workman Nydegger

(57) ABSTRACT

An orthopedic device has an elongate, tubular body defining a patella opening located generally at a center portion of the tubular body. A patella buttress including a buttress pocket is located on the tubular body and about the patella opening. The buttress pocket has various stretchability characteristics relative to the tubular body. A buttress element is associated with the buttress pocket.

15 Claims, 6 Drawing Sheets

(56) References Cited

U.S. PATENT DOCUMENTS

| | | | |
|---|---|---|---|
| 3,898,709 A * | 8/1975 | Lewis | A61F 5/0125 16/329 |
| 3,945,046 A | 3/1976 | Stromgren | |
| 4,084,584 A | 4/1978 | Detty | |
| 4,099,269 A | 7/1978 | Porner | |
| 4,116,236 A | 9/1978 | Albert | |
| 4,201,203 A | 5/1980 | Applegate | |
| D259,058 S | 4/1981 | Marshall | |
| 4,287,885 A | 9/1981 | Applegate | |
| 4,296,744 A | 10/1981 | Palumbo | |
| 4,379,463 A * | 4/1983 | Meier | A61F 5/0123 128/DIG. 15 |
| 4,425,912 A | 1/1984 | Harper | |
| D273,420 S | 4/1984 | Gruber | |
| 4,445,505 A | 5/1984 | Labour et al. | |
| 4,474,573 A | 10/1984 | Detty | |
| 4,479,272 A | 10/1984 | Beldzisky | |
| 4,607,628 A | 8/1986 | Dashefsky | |
| 4,632,106 A | 12/1986 | Gamm | |
| 4,697,583 A * | 10/1987 | Mason | A61F 5/0123 602/16 |
| 4,822,371 A | 4/1989 | Jolly et al. | |
| 4,870,956 A | 10/1989 | Fatool et al. | |
| 4,908,037 A | 3/1990 | Ross | |
| 4,941,462 A | 7/1990 | Lindberg | |
| 4,955,369 A * | 9/1990 | Bledsoe | A61F 5/0123 602/16 |
| 5,024,216 A | 6/1991 | Shiono | |
| 5,139,477 A | 8/1992 | Peters | |
| 5,154,690 A | 10/1992 | Shiono | |
| 5,168,577 A | 12/1992 | Detty | |
| 5,221,252 A | 6/1993 | Caprio, Jr. et al. | |
| 5,261,871 A | 11/1993 | Greenfield | |
| 5,263,923 A | 11/1993 | Fujimoto | |
| 5,277,697 A | 1/1994 | France et al. | |
| 5,334,135 A | 8/1994 | Grim et al. | |
| 5,367,708 A | 11/1994 | Fujimoto | |
| 5,382,223 A | 1/1995 | Springs | |
| 5,399,153 A | 3/1995 | Caprio, Jr. et al. | |
| 5,419,161 A | 5/1995 | Bodenschatz et al. | |
| 5,462,517 A | 10/1995 | Mann | |
| 5,474,524 A | 12/1995 | Carey | |
| 5,593,454 A | 1/1997 | Helmy | |
| 5,603,122 A | 2/1997 | Kania | |
| 5,643,185 A | 7/1997 | Watson et al. | |
| 5,651,847 A | 7/1997 | Loeffler | |
| 5,695,452 A | 12/1997 | Grim et al. | |
| 5,759,167 A | 6/1998 | Shields, Jr. et al. | |
| 5,792,084 A | 8/1998 | Wilson et al. | |
| 5,797,864 A | 8/1998 | Taylor | |
| 5,823,981 A | 10/1998 | Grim et al. | |
| D403,424 S | 12/1998 | Taylor et al. | |
| 5,865,166 A | 2/1999 | Fitzpatrick et al. | |
| 5,865,776 A | 2/1999 | Springs | |
| 5,865,777 A | 2/1999 | Detty | |
| D406,677 S | 3/1999 | Koschmann et al. | |
| 5,925,010 A | 7/1999 | Caprio, Jr. | |
| 5,944,682 A | 8/1999 | Milana-Panopoulos | |
| 6,063,048 A | 5/2000 | Bodenschatz et al. | |
| 6,080,121 A | 6/2000 | Madow et al. | |
| 6,149,690 A | 11/2000 | Belzidsky | |
| 6,238,360 B1 | 5/2001 | Gildersleeve et al. | |
| D444,563 S | 7/2001 | Rodgers | |
| D448,084 S | 9/2001 | Hopwood et al. | |
| 6,287,269 B1 | 9/2001 | Osti et al. | |
| D451,198 S | 11/2001 | Lamping et al. | |
| 6,551,264 B1 | 4/2003 | Cawley et al. | |
| 6,592,539 B1 | 7/2003 | Einarsson et al. | |
| D501,927 S | 2/2005 | McCormick et al. | |
| 7,004,919 B2 | 2/2006 | Gaylord et al. | |
| 7,060,045 B2 | 6/2006 | Mason et al. | |
| 7,083,586 B2 | 8/2006 | Simmons et al. | |
| D533,668 S | 12/2006 | Brown | |
| 7,217,249 B2 | 5/2007 | Scott | |
| 7,273,464 B2 | 9/2007 | Reinhardt | |
| D573,713 S | 7/2008 | Mueller et al. | |
| D574,084 S | 7/2008 | Reinhardt | |
| D618,358 S | 6/2010 | Avitable et al. | |
| 7,749,181 B2 | 7/2010 | Simmons et al. | |
| D623,756 S | 9/2010 | Chiang | |
| 7,819,830 B2 | 10/2010 | Sindel et al. | |
| D630,333 S | 1/2011 | Chiang | |
| 7,862,528 B2 | 1/2011 | Scott | |
| 7,867,183 B2 | 1/2011 | Kazmierczak et al. | |
| D634,851 S | 3/2011 | Chiang | |
| D635,267 S | 3/2011 | Chiang | |
| 7,959,590 B2 | 6/2011 | Scott | |
| D654,181 S | 2/2012 | Chiang | |
| D654,182 S | 2/2012 | Chiang | |
| 2001/0007929 A1 | 7/2001 | Schlomski | |
| 2003/0050586 A1 | 3/2003 | Domanski et al. | |
| 2003/0083605 A1 | 5/2003 | Edmund | |
| 2003/0176826 A1 | 9/2003 | Scott | |
| 2006/0069337 A1 | 3/2006 | Livolsi et al. | |
| 2006/0094999 A1 | 5/2006 | Cropper | |
| 2008/0139982 A1 * | 6/2008 | Magnusson | A61F 13/101 602/5 |
| 2008/0139985 A1 | 6/2008 | Gilmour | |
| 2008/0300524 A1 | 12/2008 | Scott | |
| 2009/0131844 A1 | 5/2009 | Dean et al. | |
| 2009/0312681 A1 * | 12/2009 | McSpadden | A61F 5/0123 602/2 |
| 2011/0137220 A1 | 6/2011 | Vollbrecht et al. | |

FOREIGN PATENT DOCUMENTS

| | | |
|---|---|---|
| DE | 3416231 A1 | 11/1985 |
| DE | 3519677 A1 | 12/1986 |
| EP | 0498062 A1 | 8/1992 |
| EP | 0835645 A1 | 4/1998 |
| EP | 1114630 A1 | 7/2001 |
| FR | 2606998 A1 | 5/1988 |
| WO | 8101240 A1 | 5/1981 |
| WO | 9101704 A1 | 2/1991 |
| WO | 2006073353 A1 | 7/2006 |

* cited by examiner

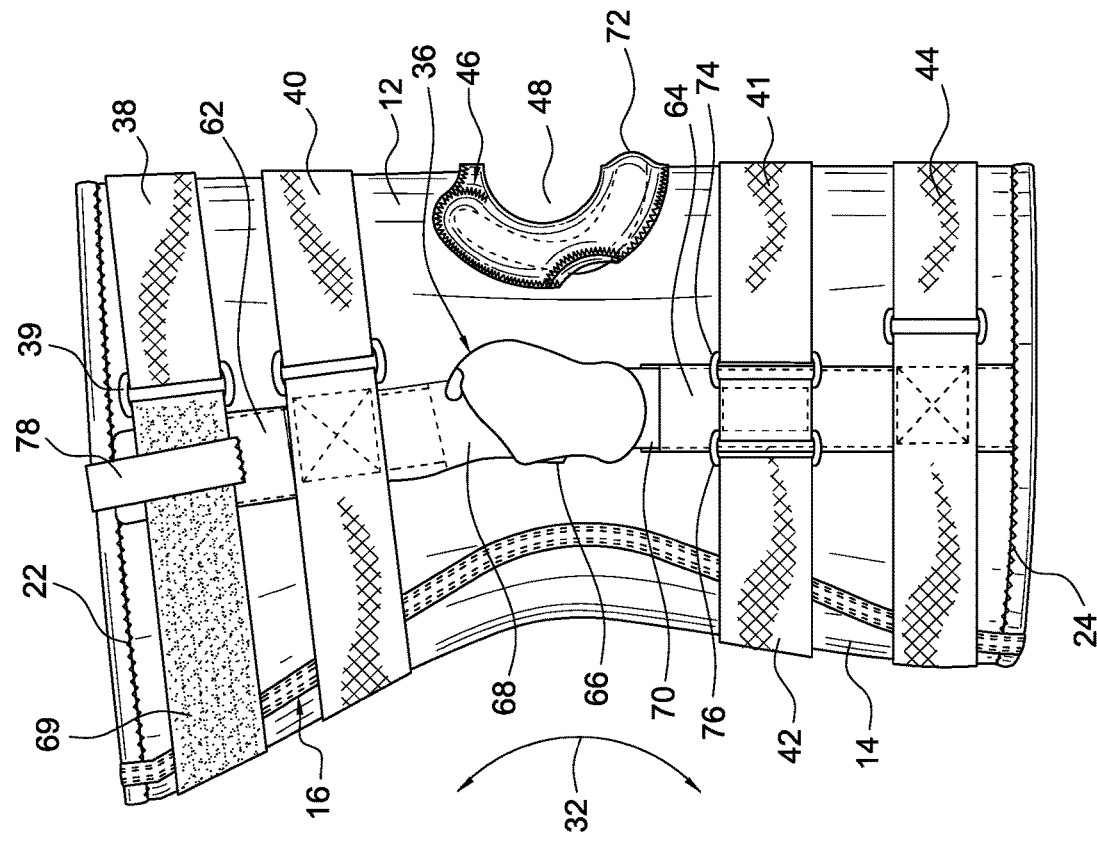
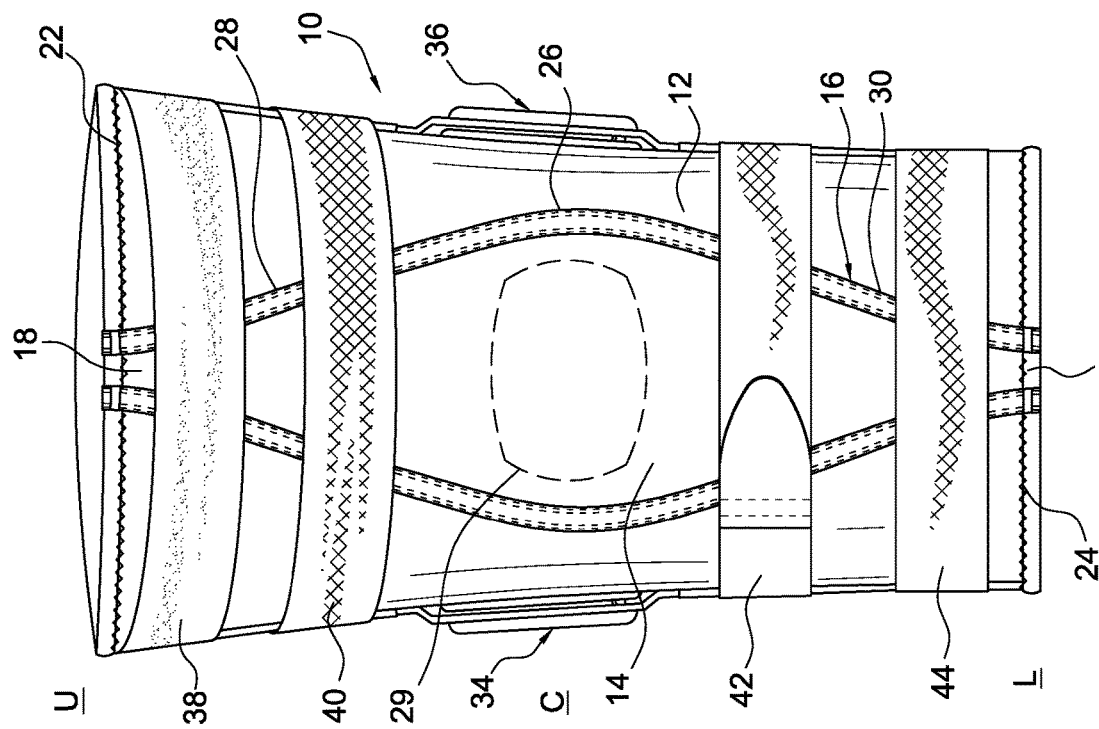
FIG. 1
FIG. 2

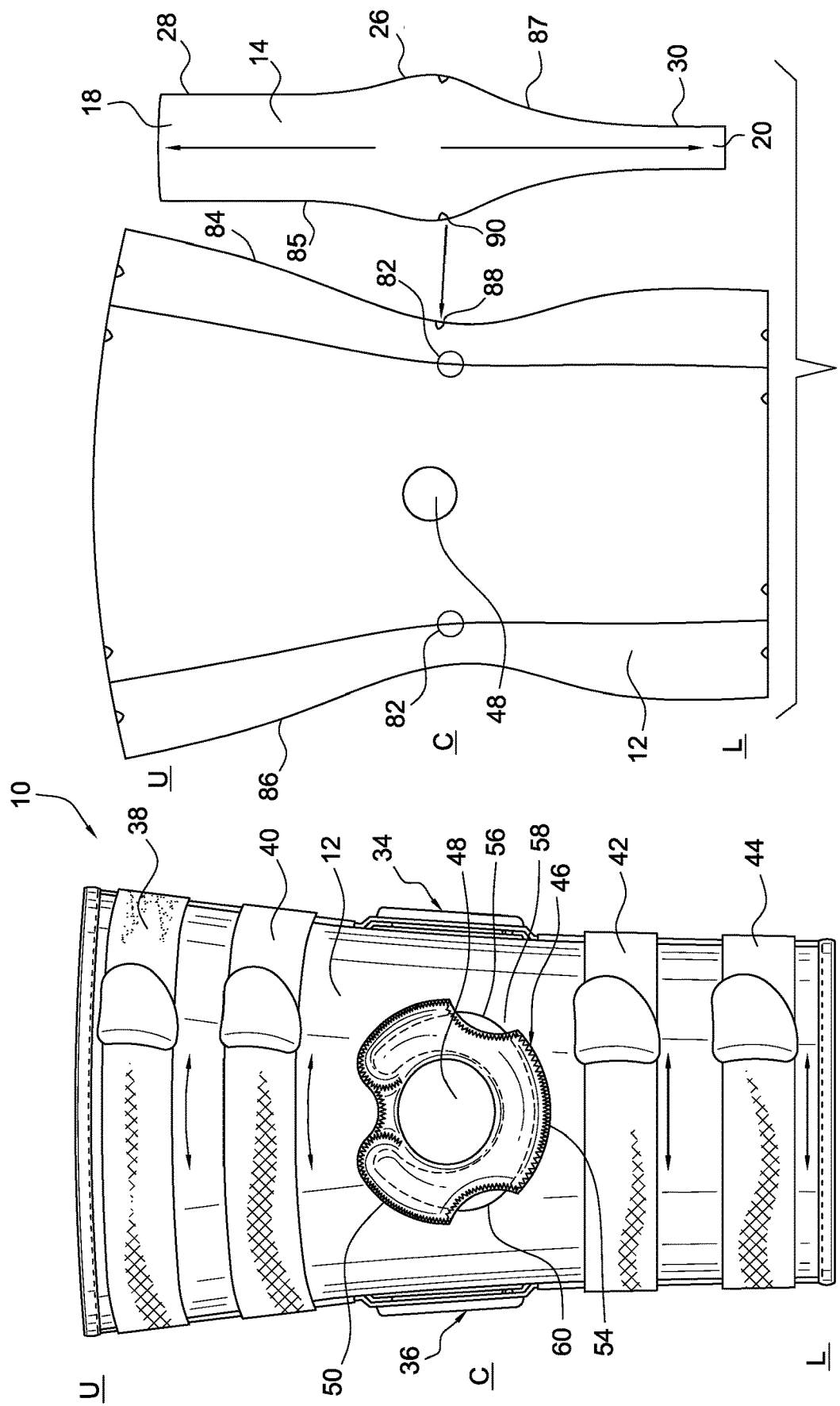

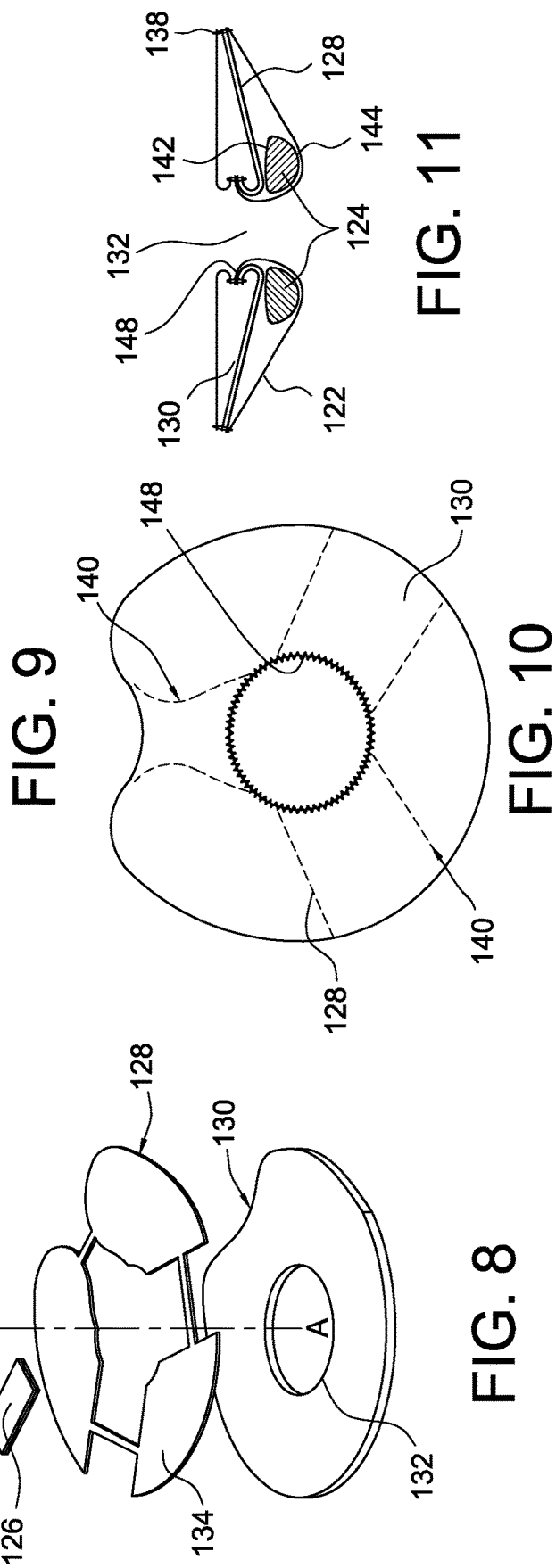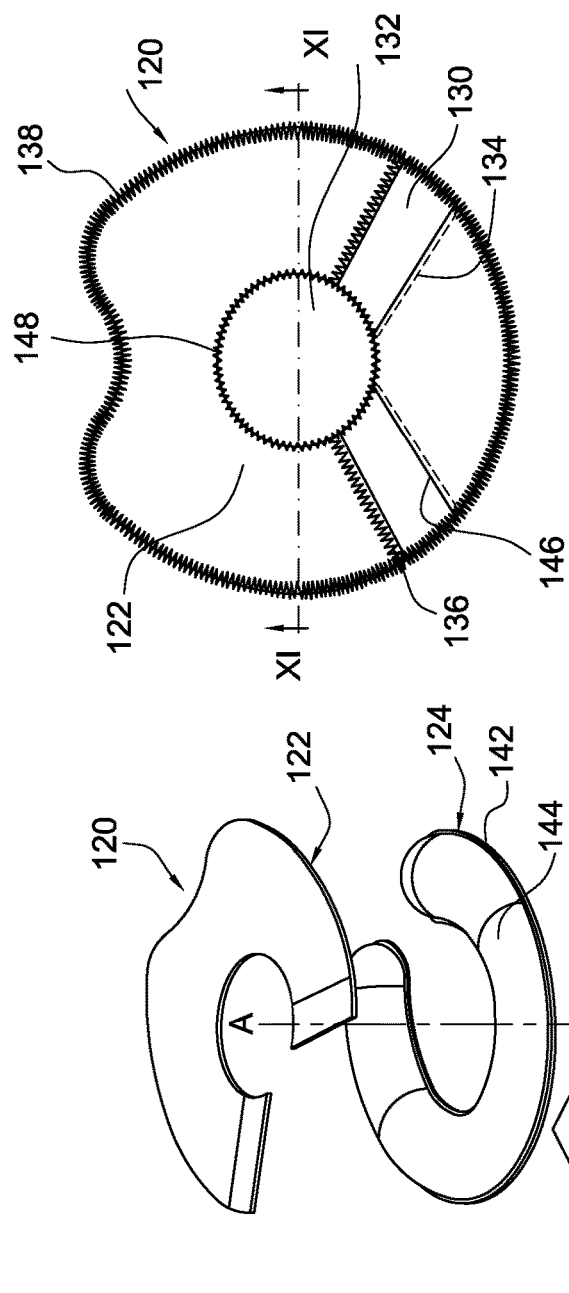

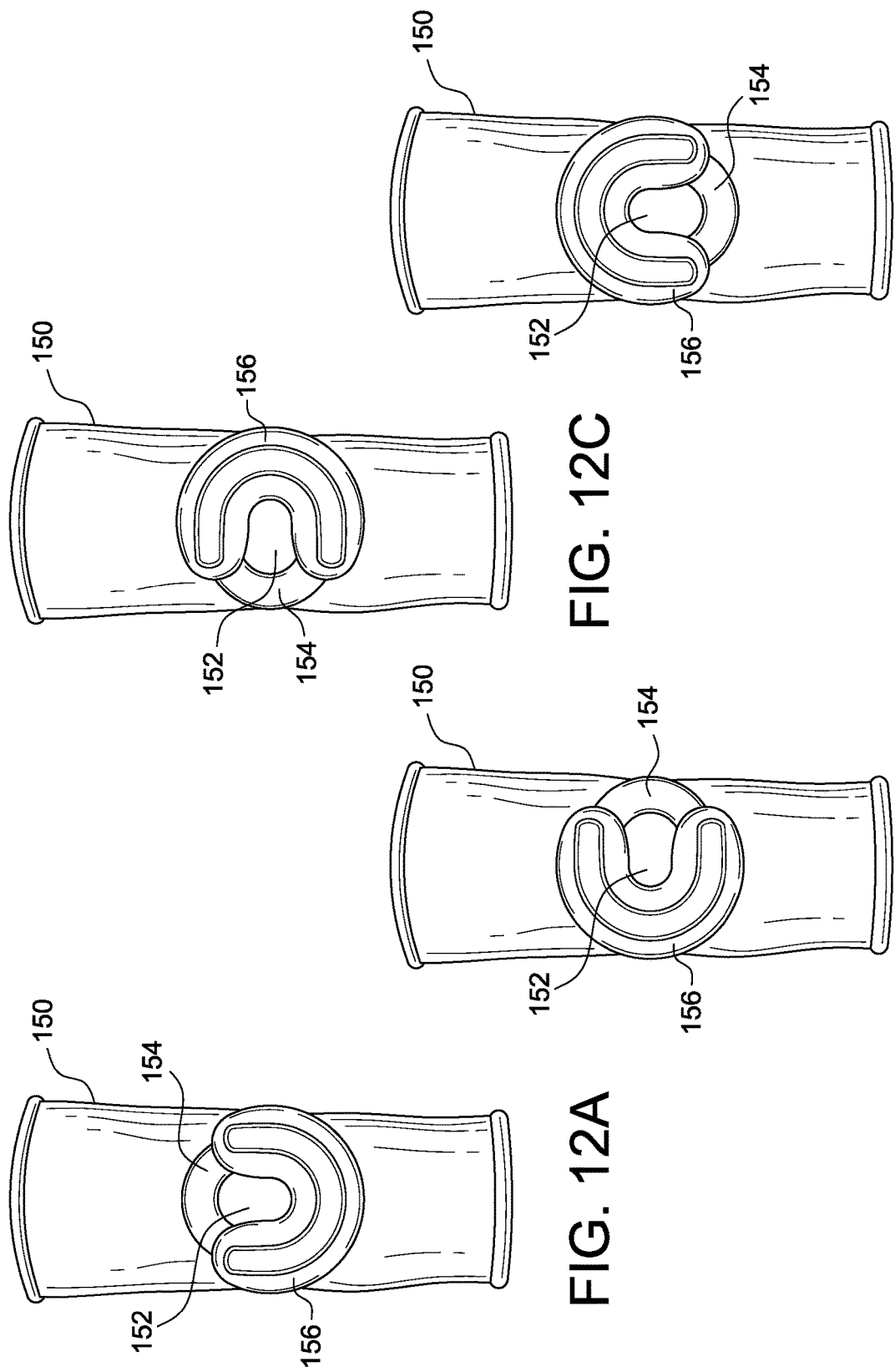

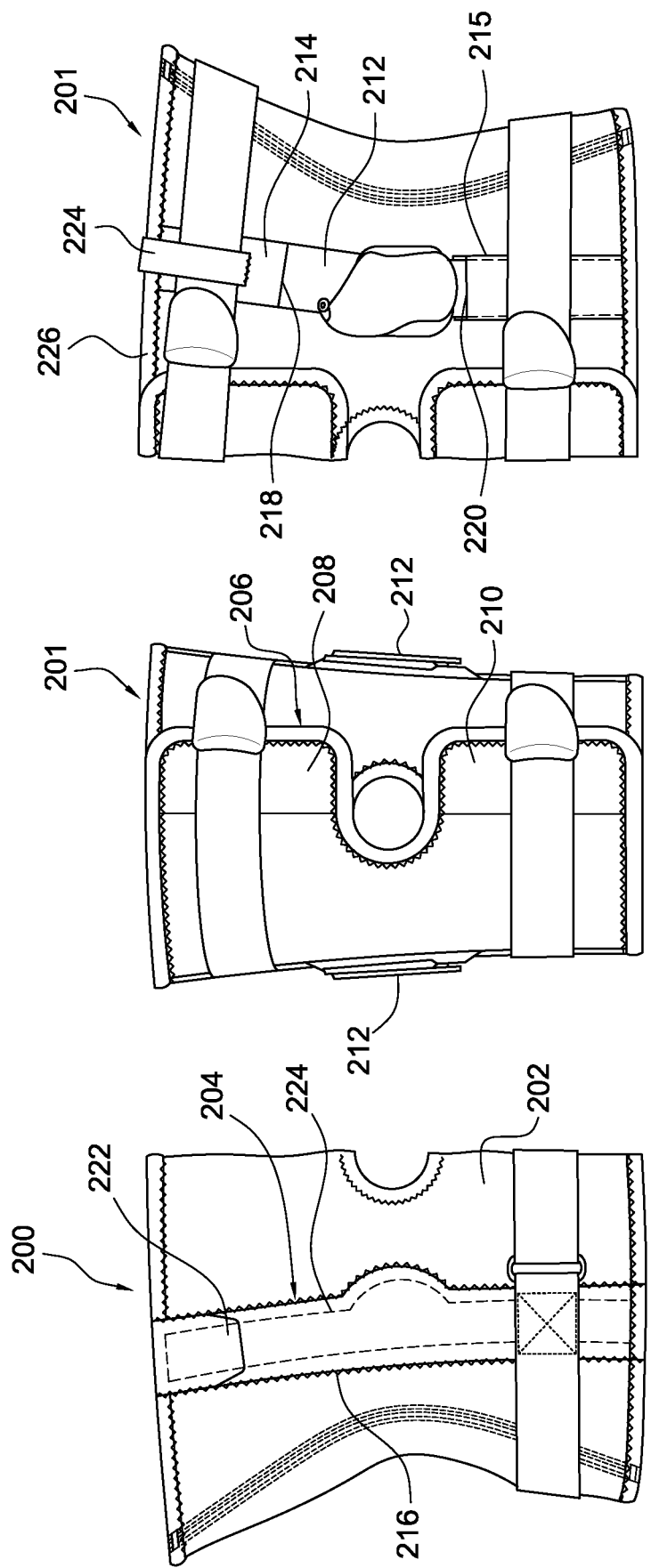

ORTHOPEDIC DEVICE

CROSS-REFERENCE TO RELATED APPLICATIONS

This application is a continuation application of U.S. utility application Ser. No. 13/331,389, filed Dec. 20, 2011, which claims the benefit of priority from U.S. provisional application Ser. No. 61/487,478, filed on May 18, 2011, and U.S. provisional application Ser. No. 61/426,188, filed on Dec. 22, 2010, the entirety of these provisional applications being incorporated herein by reference.

FIELD OF THE DISCLOSURE

This disclosure relates to an orthopedic device, and more particularly to a knee brace having at least a posterior contour adapted to a natural contour of a leg, a plurality of sections having different pretensioning, and a patella buttress for supporting a patella.

BACKGROUND

Various orthopedic devices have been developed and are available for stabilizing and protecting injured or infirm knees. Many of these supports are made from flexible resilient materials that are arranged to stretch over the knee and provide support by compression about the knee of the wearer.

Certain problems exist with many known devices in that some of the devices are formed from closed cell elastomer materials that have poor thermal conductivity and are unable to absorb or wick perspiration from the area supported by the device. These devices also have the tendency to bunch up over the popliteal region of the knee when the leg is flexed, and have seams over the popliteal region causing irritation to the wearer.

Although past efforts have been made to remedy these problems, commercially available devices typically fall short in avoiding the problems. As a result, wearers of the devices are often reluctant to consistently wear the devices, which can lead to future complications or continued discomfort.

Notably, many of these known devices provide uniform circumferential compression about the knee when the device is stretched. The compression applied by the device can be painful to the wearer if areas of the leg and knee are sensitive to pressure.

Some of the known devices include a front central opening that allow for the wearer's patella or kneecap to project. The front central opening relieves pressure that would otherwise be exerted on the patella, particularly when the knee is bent or in flexion. These devices may include a pad or buttress located about the front central opening so as to provide a restraining force to the patella and additional support, such as preventing lateral or medial displacement of the patella in the femoral groove.

Despite known solutions, many devices fail to maintain the patella pad in a proper position on the support so the opening or pad can prevent patella displacement.

Accordingly, there is a need for a knee brace that at least provides means for stabilizing and supporting the patella, as well as provide means for maintaining the brace in proper position on the leg in a comfortable manner so as not to interfere with the normal use of the leg.

SUMMARY

In accordance with the various exemplary orthopedic device embodiments of the disclosure, a knee brace is provided having a highly breathable construction for increasing patient comfort without sacrificing durability or compression of the knee brace. The knee brace can control ligament extension and flexion, and may be used to treat strains, sprains or instabilities of the anterior, medial, lateral and posterior collateral ligaments. The knee brace may also be designated for post-operative care following meniscal repairs and other reconstructive surgeries of the knee.

The various knee brace embodiments provide multiple features arranged to treat medical necessities with measurable consequences. In one example, the knee brace employs a three-dimensionally shaped contrast fabric behind the knee joint that reduces bunching, which in turn allows for greater comfort and conformance to the leg, as well as maintain compression about the leg. The contrast fabric provides for soft-tissue compression so as to offer edema control and reduce swelling.

The contrast fabric is preferably located on the posterior aspect of the knee brace, and eliminates the necessity of cutting out a section at the popliteal portion of the knee or brace, and allows for better compression over known braces having a popliteal cut-out. In particular, the knee brace is arranged to stretch in extension and relax back to a natural or predetermined shaped in flexion, thereby minimizing popliteal bunching (along the posterior side of the knee) that causes skin irritation.

Various materials and combinations thereof are employed in embodiments of the knee brace to provide for an intimate fit, reduce heat retention and sweat, and allow application of the knee brace for application from the left or right sides of the leg. These benefits are achieved by the selection of particular materials including those having breathable and quick-drying properties, stitching patterns, and pre-tensioning of certain fabric sections.

In another feature, the knee brace may include rigid uprights connected to the hinge that are malleable allowing for enhanced medial-lateral stability in a knee brace. The malleable rigid uprights also provide patient perception of enhanced stability of the knee brace. Some embodiments include pull tabs for facilitating donning and doffing of the knee brace, as well as easy fitting and maintaining the location of the hinge. Various pocket constructions are used to house the uprights and may also include the hinge as well.

In yet another feature, the knee brace may include dual lower cruciate straps that enable fine-tuned control of the anterior-posterior hinge placement and cinch the knee brace above the gastroc to reduce migration of the brace over the leg. Additionally, the knee brace includes a reversible strapping system by way of individual straps for both the anterior and posterior aspects of the leg. This enables the brace to be set up to pull laterally-to medially, medially-to-laterally, or a combination of both, depending on specific treatment objectives of the wearer of the knee brace.

Certain patella buttresses may be used in combination with embodiments of the knee brace. According to various embodiments described herein, the buttress may employ various textile combinations having different properties and locations which lead to improved support about the buttress. Certain patella buttresses are located on the exterior surface of the knee brace, as opposed to on a posterior surface as in known braces. These embodiments include the concept of providing an intermediate layer lacking stretchability so as to prevent excessive stretching of the buttress and effectively yielding to the movement of the wearer without providing adequate support.

Alternatively, patella buttress embodiments may be arranged to direct a buttress toward the knee or be arranged with a combination of materials and stitching types to minimize or enhance localized stretching of the patella buttress and particularly direct the buttress.

In yet another embodiment, the patella buttress may be securable about an opening formed by the knee brace. The patella buttress is configured and dimensioned so that it can be removably mounted at a plurality of locations about the circumference of the opening, thereby allowing the wearer to place the patella buttress at a location best suited for supporting an individual wearer's patella.

BRIEF DESCRIPTION OF THE DRAWINGS

The numerous other advantages, features and functions of embodiments of a knee brace and orthopedic concepts will become readily apparent and better understood in view of the following description and accompanying drawings. The following description is not intended to limit the scope of the knee brace and orthopedic concepts, but instead merely provides exemplary embodiments for ease of understanding.

FIG. 1 is a rear elevational view showing a knee brace embodiment including certain features of the orthopedic device.

FIG. 2 is a side elevational view showing the knee brace of FIG. 1.

FIG. 3 is a front elevational view showing the knee brace of FIG. 1.

FIG. 4 is a perspective view showing size relationships of a main body panel and a posterior panel in the knee brace of FIG. 1.

FIG. 8 is an exploded view of another embodiment of a patella buttress from the inside surface descending to the outside surface.

FIG. 9 is a rear, inside surface view of the patella buttress of FIG. 8.

FIG. 10 is an outside surface view of the patella buttress of FIG. 8 without the innermost layer and the buttress.

FIG. 11 is a cross-sectional view taken along line XI-XI in FIG. 9.

FIGS. 12A-12D show an embodiment of the knee brace wherein the patella buttress is adapted to be arranged at a plurality of orientations along an interior surface of and about an opening of the knee brace.

FIG. 13 is a side elevational view showing another embodiment of a knee brace having a hinge secured within a pocket.

FIG. 14 is a front elevational view showing another embodiment of a knee brace with a set of hinges having portions exposed on the outer surface of the knee brace.

FIG. 15 is a second side elevational view showing the knee brace of FIG. 14.

Figure 7:
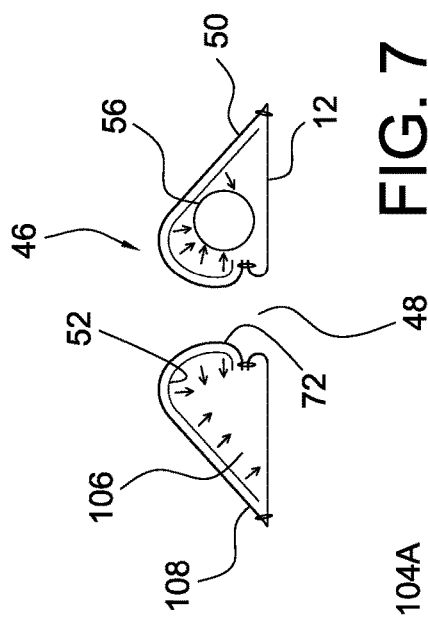
FIG. 7 is a cross-section view taken along line VII-VII of the patella buttress of FIG. 5.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a knee brace, and in no way limit the structures or configurations of a liner thereof according to the present disclosure.

DETAILED DESCRIPTION OF VARIOUS EMBODIMENTS

A. Overview

Numerous knee brace embodiments and components for use therewith are described herein, with particular focus given to supports and components directed to the knee joint and surrounding areas. The knee brace embodiments may serve in protective, preventative or remedial capacities. While the knee brace is described within the context of preferred embodiments that are directed to supporting a knee joint, many of the features described herein may be extended to other supports and components that bear or secure other joints and body parts, such as the wrist, elbow, shoulder, ankle and neck.

The knee brace embodiments and components for use therewith may be dimensioned to accommodate different types, shapes and sizes of human joints and appendages. These embodiments may be modified to orient principal forces exerted by the leg.

As is well understood, the primary movements of the knee comprise flexion, i.e., rearward rotational movement of the tibia relative to the femur, and extension, i.e., forward rotational movement of the tibia relative to the femur.

For explanatory purposes, each knee brace or component thereof described herein may be divided into sections which are denoted by general anatomical terms for the human body. Such anatomical terms are provided to distinguish various elements of the leg support embodiments from one another, but which are not to be considered to limit the scope of the invention.

The terms "proximal" and "distal" generally refer to locations of the knee brace that correspond to the location of leg relative to the point of attachment of the leg to the body. The terms "upper" and "lower" may be used in combination with "proximal" and "distal" to connote gradations in location of "proximal" and "distal." The location at where the support corresponds to the knee joint is used herein to generally delimit the proximal and distal, or upper (U) and lower (L) sections spaced by a center section (C) of the knee brace.

The embodiments of the leg support can also be considered to fall within "anterior" and "posterior" sections by an anterior-posterior plane. The anterior-posterior plane generally corresponds to the coronal or frontal plane of a human leg which lies along the central longitudinal axis of a body. A posterior side or element is therefore located behind this anterior-posterior plane, whereas an anterior side or element is located in front of the anterior-posterior plane.

The terms "inwardly" or "inner" commonly used herein to distinguish the side of the leg support that may be directed to the posterior side of the support and specifically adjacent to the leg of the wearer of the support. On the other hand, the term "outwardly" or "outer" are used to denote the side of the support that is opposite to the inwardly side.

The terms "medial" and "lateral" are relative terms that are generally understood as indicating location near the midsaggital plane or midline. Therefore, elements that are located near the midline are referred to as "medial" and those elements that are further from the midline are considered to be "lateral." The term "central" is used to denote the area along the midline including portions of the medial and lateral regions.

B. Various Embodiments

FIGS. 1-3 illustrate an embodiment of the knee brace 10. The knee brace 10 includes a main body panel 12 and a posterior panel 14. The posterior panel 14 is secured to the main body panel 12 along its longitudinal length by longitudinal seams 16 such as inner and outer parallel seams located on both lateral and medial sides of the knee brace. The main body panel and the posterior panel together form an elongate, tubular body adapted to anatomically conform to the thigh, knee and calf, with the main body panel generally forming a curved or arcuate cross-section. The brace flares at the thigh or upper portion (U) of the brace and tapers below the knee or central (C) to the calf or lower portion (L).

The knee brace resembles a leg in extension when in a rest or unworn condition. The posterior panel 14 is pretensioned or has greater tensioning relative to the main body panel 12 which may or may not have any particular pretensioning. From the tension of the posterior panel 14, the knee brace has a posterior contour 32 that reflects a natural shape of a leg in extension. By virtue of the tension of the posterior panel 14, the knee brace also defines upper and lower inclined edges 22, 24, sloping downwardly from the anterior aspect of the knee brace to the posterior aspect of the knee brace.

The posterior panel 14 defines upper and lower portions 28, 30 that space the entirety of opposed sides of the main body panel 12 from one another. The upper and lower portions 28, 30 narrow toward the upper and lower edges 22, 24 from a larger center portion 26. The upper and lower portions 28, 30 have a sufficient spacing width 18, 20 from the main body panel that allows for a portion of the posterior panel 14 to form part of the upper and lower edges 22, 24. This spacing width 18, 20 forms a clearance between opposed sides of the main body panel, and minimizes any unraveling of the stitching securing the posterior panel to the main body panel. The spacing width further eliminates any potential pressure points by gradually and evenly distributing pressure on the posterior aspect of the leg.

The center portion 26 generally corresponds to the popliteal of a wearer's knee. The configuration of the posterior panel 14 removes the need to for a single seam located along the posterior center of the brace and minimizes patient irritation on the popliteal area of the wearer's knee. Alternatively, the knee brace may be provided with a popliteal opening 29 that corresponds to the popliteal section of the knee brace. The popliteal opening is preferably, but not limited, to be formed by the posterior panel 14, and may have its periphery reinforced with stitching or other means such as an additional fabric edging so as to mitigate fraying about the opening.

The knee brace includes first and second hinges 34, 36 located on lateral and medial sides of the brace. The hinges 34, 36 have upper and lower struts 68, 70 extending from opposed sides of a hinge mechanism 66 that are retained on the main body panel by upper and lower pockets 62, 64. The struts 68, 70 may be formed from a malleable material, such as aluminum, that allows for some customization to the wearer's body shape, while remaining sufficiently strong to avoid bending while the knee brace is in use by the wearer.

As depicted in FIG. 3, the hinge mechanism 66 may be adjustably secured to the main body panel 12 at fastening points 82 so that the placement of the hinge mechanism can be shifted either posteriorly or anteriorly for anterior-posterior placement. This allows for the hinge to be placed at a particular location, and permits some minor adjustment to secure the hinge mechanism anteriorly or posteriorly at particular locations. For example, at an initial fitting by a clinician, the hinge location is set according to the particular anatomy of the patient because the strap is locked by the hook on both sides and the patient does not have to adjust this again. This allows for repeated and consistent donning.

The brace depicted in FIGS. 1-3 is considered a long version of the knee brace (a shorter version is found in FIGS. 8-10). The knee brace may include a plurality of circumferential straps. The straps may include an upper thigh strap 38 having a strap loop or pull tab 78 for guidance, a lower thigh strap 40, and a lower calf strap 44. Each of the straps may be removable to allow for the brace to be customized to the patient for directional leverage.

For example, the upper thigh strap 38 is removably mounted on the outer surface of the hinge cover 62, such as by a hook and loop system, and includes a buckle 39 at one end. The strap 38 can be reversed in orientation, meaning the direction of the pull of the strap. This reversible strapping system allows the brace to be set up to pull laterally-to-medially, medially-to-laterally, or a combination of both, as exemplified in FIG. 3 by the arrows under the various straps, by modifying the orientation of the upper thigh strap 38 relative to the lower thigh strap 40.

The brace may include separate anterior and posterior straps 41, 42 located along any portion of the knee brace. For example, the brace may have an anterior strap 41 that extends only about the anterior side of the brace. The anterior strap is secured to buckles 74 located on lateral and medial sides of the brace. A posterior strap 42 extends only about the posterior side of the brace, and is secured to buckles 76 located on lateral and medial sides of the brace. Because the hinge mechanism has anterior-posterior placement, the anterior posterior straps 41, 42 have fine-tuned control thereby allowing the knee brace to be cinched above the wearer's gastroc to reduce migration.

As shown in FIG. 4, the posterior panel 14 is sized shorter than the main body panel 12 prior to securing the panels to one another. The main body panel 12 has longitudinal edges 84, 86 along which longitudinal edges 85, 87 of the posterior panel 14 respectively secure. The main body panel 12 has an affixation point 88 upon which a corresponding affixation point 90 of the posterior panel 14 secures.

The posterior panel 14 is sewn along the longitudinal edges to the main body panel 12 from the upper portion 28 to the center portion 26, particularly to the affixation points 88, 90. The posterior panel 14 is then sewn from the center portion 26 to the lower portion 30. From this configuration, tension is formed in the posterior panel 14, and imparts the natural contour 32 to the shape of a knee in a naturally bent position. The affixation points 88, 90, serve as a point of inflection for the natural contour 32 about the center or knee portion of the brace. This natural contour shape is in contrast to the conical shape of conventional tubular braces. The tensioning of the posterior panel will also reduce material bunching behind the knee whether the knee is in flexion or extension.

According to one variation, the material forming the posterior panel is thinner than the material forming the main body panel prior to being secured to the main body panel. This variation allows for a more stretchable posterior panel. According to another variation, the material forming the posterior panel has the same thickness as the material used to form the main body panel.

The posterior panel may have the same stretch properties as the main body panel so as to avoid sharp wrinkles behind the knee that may cause irritation. When the posterior and main body panels have the same stretch properties, the knee brace can provide a more consistent or even circumferential compression. It follows that if the posterior panel is easier to stretch than the main body panel, the posterior panel may tend to stretch to its maximum width before the main body panel has stretched sufficiently to provide necessary compression.

The material used to form the main body and posterior panels is preferably a three-dimensional double faced spacer material having a circular knit. The knit of the spacer material is linked which allows for a gradual stretch until there is a complete extension of the material and hence the brace itself. The spacer material has high breathability that allows sweat to evaporate and heat to dissipate. The breathability of the spacer material provides an environment inhospitable to bacteria growth. The spacer material moves with the body, and does not cause unneeded resistant to range of motion. The spacer material is preferably latex and neoprene free, and therefore the material may form the entire thickness of the brace without additional layers.

The spacer material is constructed with a fine gauge yarn and has a tight knit pattern leading to a smooth finish that is cool to the touch and is comfortable for wear. In many known knee braces, typical materials are manufactured with thicker yarns and looser knit patterns having a coarse texture that leads to skin irritation or discomfort.

The material construction of the main body panel and posterior panel of the knee brace in accordance with the embodiments herein is particularly advantageous in that it facilitates donning and doffing of the brace. The main body and posterior panels preferably are placed in contact with the skin of the wearer, and there is sufficient friction to maintain the brace against the skin of the wearer without the brace sliding off the leg.

Because the spacer material has natural compressibility, the brace is preferably provided without additional foam padding along either the outer or inner surfaces of the main body panel. This allows for improved breathability over known knee braces thereby minimizing sweat and heat build-up, and also has improved air permeability so as to reduce moisture and bacteria accumulation.

Figure 6:
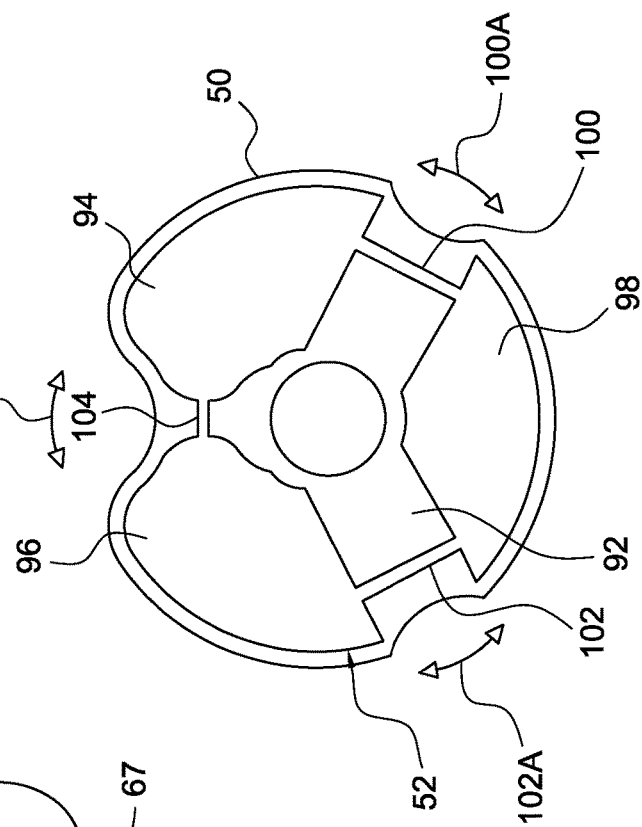
FIG. 6 is a schematic view showing an inner surface of the patella buttress of FIG. 5.
Figure 5:
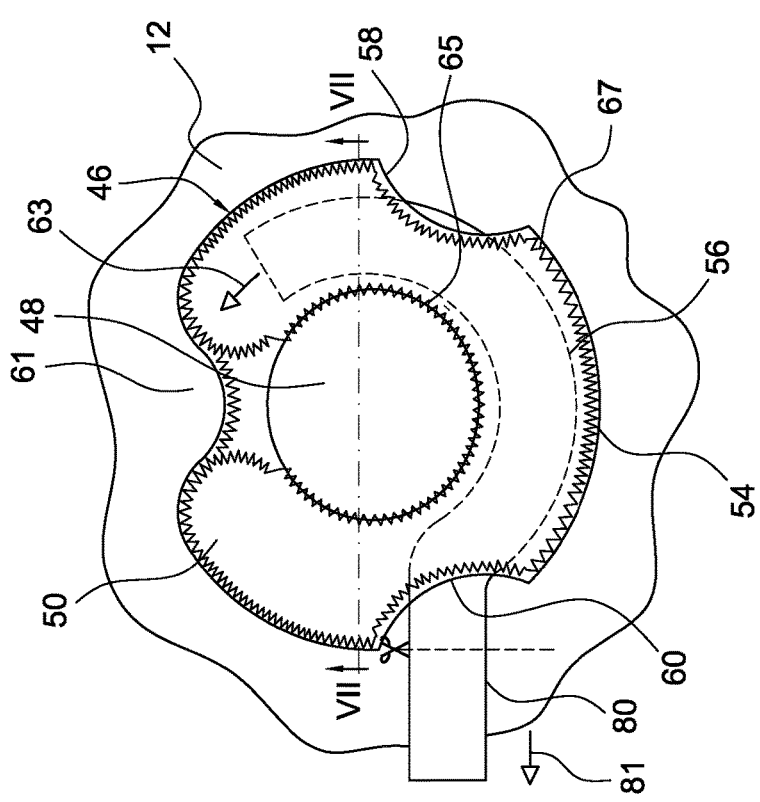
FIG. 5 is a sectional view showing an embodiment of a patella buttress in the knee brace of FIG. 1.

The patella buttress is depicted in greater detail in FIGS. 5-7. The buttress 46 surrounds a patella opening 48 formed by the main body panel 12. The buttress 46 includes an outer covering 50, an intermediate layer 52 secured to an inner surface of the outer covering 50, and a buttress element or flexible rod 56. The outer covering 50 and the intermediate layer 52 are secured to the main body panel 12 about their inner and outer peripheral edges by a stitching (preferably a zigzag formation) to allow for some stretching of the buttress 46 relative to the main body panel 12. The combination of the outer covering 50 and intermediate layer 52 forms a pocket 106 between the main body panel 12, and the rod 56 is securely located within the pocket 106.

The outer covering 50 forms first and second apertures 58, 60 located on opposed sides of the buttress 46. The apertures 58, 60 allow for access to the rod 56, whereby a portion of the rod 56 can be removed for modification. For example, in an initial configuration, the rod 56 generally conforms to the shape of a horseshoe. The rod 56 can be pulled in a direction 81 from the aperture 60 and have an end portion 80 severed so as to reduce its length. The rod 56 is then pulled in another direction 63 toward a top portion 61 of the buttress so as to form a J-shape. The J-shape or lateral "J" is a shape that allows for a greater concentration of support about the patella. From the two apertures 58, 60, either side of the rod can be configured to form the J-shape.

The intermediate layer 52 has a configuration of multiple zones that are located about the pocket 106 of the buttress. In the illustrated example, the intermediate layer 52 has first side zone 94, second side zone 96 and lower zone 98. Each of the zones 94, 96, 98 is preferably connected to one another by a tether 100, 102, 104, and spaced by a clearance 92 that maintains the zones in proper spacing with one another. The zones are arranged to minimize or inhibit stretching of the length, width, and expansion of circumference of the outer layer relative to the main body panel.

The top portion 61 of the buttress is shaped so as to better contour and adapt to the shape of patella in order to reduce stretch of the buttress (as evidenced by the shorter tether 104 than tethers 100, 102). This will reduce the stretch of the buttress so it does not bow significantly radially outwardly and thereby better and stably hold the rod about the knee of the wearer. The rod is preferably formed from a silicone closed-cell sponge cord, however is may be constructed from other suitable materials that can be used to support the patella in a similar fashion to a silicone closed-cell sponge or foam insert.

As depicted in FIG. 7, the buttress 46 forms a bulge 72 (seen also in FIG. 2) about the periphery of the opening 48, whereby a portion of the outer covering 50 and the intermediate layer 52 wraps about the rod around the periphery of the opening 48. From this construction, the intermediate layer limits stretching of the opening 48 in order to securely retain the patella of the wearer. The buttress 46 gradually tapers from the bulge 72 to the outer peripheral edges 108 of the outer covering 50 and intermediate layer 52.

The outer layer is preferably formed from the same material used to form the main body panel. The intermediate layer may be formed from a material that has little or no stretchability, such as a rigid textile. The lack of stretchability of the intermediate layer prevents excessive stretching of the buttress so as to prevent the buttress from stretching too much and effectively yielding to the movement of the wearer without providing adequate support.

For example, the intermediate layer directs the rod inwardly toward the patella of the wearer, effectively drawing the rod toward the patella despite movement by the wearer (as evidenced by arrows in FIG. 7). In areas of the buttress without the rod, as shown in FIG. 7, these areas are also reinforced by the intermediate layer so as to inhibit stretching outward relative to the patella of the wearer.

In the illustrated three zone construction in FIG. 6, the intermediate layer is configured to achieve the desired stretch properties within the buttress. The zones are strategically located to provide a combination of optimal stretch and direct a posterior force toward the patella in critical areas. The tethers 100, 102, 104 may allow for some radial stretching of the buttress, as depicted by arrows 100A, 102A, 104A, thereby permitting some radial adjustment of the buttress about the patella of the wearer, whereas the zones inhibit radial stretching due to their larger material portions, as evidenced by FIG. 6.

Variations of the stitching may be configured such that in areas including the stitching 65 about the opening 48, the stitching is in a looser zigzag formation in order to allow for some stretching of the opening 48, whereas the stitching 67 on the outer periphery 54 of the buttress is tighter, whether or not it is in a zigzag configuration, so as to inhibit stretching of the outer periphery 54 of the buttress. Of course, even on the outer periphery stitching 67, the tightness of the stitching may be varied if more stretching is desired, such as providing a looser stitching at the apertures 58, 60.

In another embodiment of the patella buttress, FIGS. 8-11 show an alternative patella buttress 120 that allows for removal of patella buttress from the inside of the knee brace.

As shown in FIG. 8, the patella buttress includes an inner layer 122 having a horseshoe configuration oriented oppositely in direction to the horseshoe shaped buttress 124. A fastener material 126 is removably securable to the buttress 124 and an interlining or intermediate layer 128. An outer layer 130 forms an opening 132 that is axially aligned along axis A-A with the inner layer 122, the buttress 124, and the intermediate layer 128. The outer layer may be a separate layer from the main body panel, or may merely be the main body panel described in connection with the embodiment of FIGS. 1-3.

The inner layer 122 is preferably formed from a stretchable jersey type fabric, thereby allowing the buttress 124 to yield toward the knee of a wearer. The buttress 124 is shaped by having a generally flat surface 142 that faces the outer layer 130 or outermost surface of the knee brace. The buttress has a rounded surface 144 that is oriented toward the inner layer 122, and may be constructed from any suitable material providing compressibility, such as foam with a textile covering.

The intermediate layer 128 is preferably non-stretchable, as in the intermediate layer described above in connection to the embodiment of FIGS. 5-7. Further, the intermediate layer 128 may be formed from or include an unbroken loop material 134 thereby permitting the fastener material 126 to be secured thereon.

According to FIG. 9, the inside surface of the patella buttress 120 is shown generally as it would appear in the knee brace. The inner layer 122 is oriented oppositely to the buttress 124 so as to form an opening 146 between the intermediate layer 128 and likewise the outer layer 130 and define a pocket for retaining the buttress 124 at stitching 136 located on opposed sides of the opening 146.

The stitching 148 around the opening 132 is provided more tightly than the outer edge stitching 138 around the inner layer and the stitching 136. For example, the stitching 148 may be a zigzag stitching having 11-13 stitches per 3.0 cm. On the other hand, the stitching 136, 138 may also be a zigzag stitching having 9-11 stitches per 3.0 cm, which is looser than the stitching 148 and allows for more stretching, thereby allowing the buttress to flex outwardly relative to the opening.

In reference to FIG. 10, the intermediate layer 128 is secured to the outer layer 130 by a single needle stitch which generally prevents flexing of the intermediate layer 128. Suitable stitching may be used to secure the intermediate layer 128 to the outer layer 130, or alternatively, the intermediate layer may be laminated or otherwise adhered to the outer layer.

Turning to FIG. 11, the outer layer 130 has greater padding or cushioning toward the opening 132 in part due to the outer layer 130 being less or not compressed at this location. The outer layer is more compressed as it approaches the outer edge stitching 138. The buttress 124 is biased toward the inside of the brace or wearer's knee, with the rounded surface 144 being directed toward the inside of the brace.

From the stitching types, and the material properties of the various layers, the patella buttress provides ample compression about the knee, while allowing for some accommodation of stretching in certain directions while inhibiting stretching in other directions.

The basic principles described herein in regard to using materials having different properties and different stitching patterns and stitches per cm may be employed in any of the aspects of the knee brace to either inhibit or enhance stretchability.

As illustrated in FIGS. 12A-12D, an alternative embodiment of patella buttress 156 is shown that is adjustably and removable secured to an inner surface 150 of the knee brace about the circumference of a patella opening 152 formed thereby. The border 154 has a loop material that can engage hook material located along a surface of the buttress 156. FIGS. 12A-12D exemplify how the buttress 156 can be attached to the inner surface 150 of the knee brace among a plurality of orientations. Moreover, if it is not desired to include the buttress, it can be easily removed without significantly interfering with the remainder of the brace. The buttress may be formed from a variety of materials such as foam, and may include a suitable cover. It may also be trimmed according to the needs of the wearer.

Turning to the embodiments of FIG. 13, a short version of the knee brace 200 may be provided with a hinge retainer 204 that conceals one of the lateral or medial hinges. The hinge retainer 204 includes a main pocket 216 and a flap 222 that covers the proximal end (or alternatively the distal end) of the main pocket 216. The main pocket 216 is formed so as to snugly accommodate the hinge 224.

The knee brace 200 is configured as a "wraparound" brace by being adapted to wrap about the leg of the wearer with a wrap configuration 206 having wrap tabs 208, 210 that secure to a main body 202 of the brace 200. The strap tabs 208, 210 are located above and below the knee of the wearer so as to provide additional circumferential tightening of the knee brace.

FIGS. 14-15 shows an alternative knee brace embodiment 201 of the knee brace 200 of FIG. 12 wherein portions of the hinges 212 are exposed on the outer surface of the brace, such as instances wherein the hinges are range-of-motion hinges requiring adjustment. The hinges 212 are secured similarly as shown in connection with the knee brace embodiment 10 of FIGS. 1 and 2. Particularly, the hinges 212 are retained by pockets 214, 215, and having openings 218, 220 for receiving arms of the hinges 212.

The knee brace 201 includes a strap loop or pull tab 224 that serves the dual purposes of retaining a strap, and as a tab for assisting in the donning of the knee brace. Particularly, the pull tab 224 does not extend or only minimally extends beyond the proximal end 226 of the main body 202 so as to avoid interfering or catching on any objects. The pull tab 224 may be connected to the main body 202 by zigzag stitching to allow and formed from a stretchable material to allow for some stretching as the wearer dons the brace.

It should be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Those skilled in the art will recognize the interchangeability of various disclosed features. In addition to the variations described herein, other known equivalents for each feature can be mixed and matched by one of ordinary skill in this art to construct suspension liner in accordance with principles of the present invention.

Although this invention has been disclosed in the context of certain exemplary embodiments and variations thereof, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A knee brace, comprising:
a main body panel, the main body panel having a first and a second affixation point arranged in a center portion of first and second longitudinal edges of the main body panel;
a posterior panel sized shorter than the main body panel when in an untensioned configuration, the posterior panel having a first affixation point and a second affixation point each arranged in a center portion of first and second longitudinal edges of the posterior panel, respectively, the posterior panel secured to the main body panel at the corresponding first and second affixation points of the main body panel and tensioned along a longitudinal length of the main body panel such that an upper edge of the posterior panel is aligned with an upper edge of the main body and a lower edge of the posterior panel is aligned with a lower edge of the main body panel, the main body panel and the posterior panel together forming an elongate, tubular body adapted to anatomically conform to a thigh, knee and calf, with the main body panel generally forming a curved or arcuate cross-section; and
first and second hinges located on lateral and medial sides of the knee brace, respectively, the first and second hinges each having upper and lower struts extending from opposed sides of a hinge mechanism, the main body panel including first and second hinge pockets on each of the lateral and medial sides, each hinge mechanism being retained by the main body panel by the first and second hinge pockets, respectively;
wherein the first and second longitudinal edges of the main body panel and the posterior panel when tensioned from the shorter, untensioned configuration form first and second longitudinal seams that are posterior to the first and second hinge pockets;
wherein, unworn, the posterior panel forms a posterior contour having a curved configuration such that the first and second affixation points of the posterior panel and main body panel form a point of inflection for the posterior contour located about a knee portion of the brace.

2. The knee brace of claim 1, wherein upper and lower portions of the posterior panel narrow from a center of the posterior panel toward the upper and lower edges of the posterior panel, respectively.

3. The knee brace of claim 2, wherein the upper and lower portions of the posterior panel have first and second widths such that the first and second widths form the upper and lower edges of the posterior panel and upper and lower clearances between opposed sides of the main body panel.

4. The knee brace of claim 2, wherein the upper and lower portions of the posterior panel space an entirety of opposed sides of the main body panel from one another.

5. The knee brace of claim 1, further comprising a patella opening and a patella buttress secured to the main body panel about the patella opening.

6. The knee brace of claim 5, wherein the patella buttress is adjustably and removably secured to an inner surface of the main body panel about a circumference of the patella opening.

7. The knee brace of claim 1, wherein the posterior panel comprises a center arranged to correspond to a popliteal of the knee.

8. The knee brace of claim 1, wherein the main body panel is untensioned relative to the posterior panel when the posterior panel is secured to the main body panel.

9. The knee brace of claim 1, wherein the knee brace also defines an upper inclined edge sloping downwardly from an anterior aspect of the knee brace to a posterior aspect of the knee brace.

10. The knee brace of claim 1, further comprising at least one strap removably mounted on an outer surface of one of the first and second hinge pockets and passes through a strap loop located on the one of the first and second hinge pockets, the at least one strap arranged for extending circumferentially about the knee brace and arranged for being reversed in circumferential orientation in either a laterally-to-medially or medially-to-laterally orientation.

11. The knee brace of claim 1, further comprising at least one of anterior or posterior straps extending only about anterior or posterior sides of the knee brace, respectively, the at least one of anterior or posterior straps securing to first and second buckles located on the lateral and medial sides, respectively, of the knee brace.

12. A knee brace, comprising:
a main body panel, the main body panel having a first and a second affixation point arranged in a center portion of first and second longitudinal edges of the main body panel;
a posterior panel having a first affixation point and a second affixation point arranged in a center portion of first and second longitudinal edges of the posterior panel, respectively, the posterior panel secured to the main body panel at the corresponding first and second affixation points of the main body panel and along a longitudinal length of the main body panel, the main body panel and the posterior panel together forming an elongate, tubular body adapted to anatomically conform to a thigh, knee and calf, with the main body panel generally forming a curved or arcuate cross-section; and
first and second hinges located on lateral and medial sides of the knee brace, respectively, the first and second hinges each having upper and lower struts extending from opposed sides of a hinge mechanism, the main body panel including first and second hinge pockets on each of the lateral and medial sides, each hinge mechanism being retained by the main body panel by the first and second hinge pockets, respectively;
wherein, unworn, the posterior panel forms a posterior contour having a curved configuration such that the first and second affixation points of the posterior panel and main body panel form a point of inflection for the posterior contour located about a central knee portion of the brace;
wherein the posterior panel is sized shorter than the main body panel when in an untensioned configuration;
wherein the first and second longitudinal edges of the main body panel respectively secure to the first and second longitudinal edges of the posterior panel when the posterior panel is tensioned by increasing in length from the untensioned configuration;
wherein the first and second longitudinal edges of the main body panel and the posterior panel when tensioned from the shorter, untensioned configuration form first and second longitudinal seams that are posterior to the first and second hinge pockets;

wherein upper and lower portions of the posterior panel narrow from a center of the posterior panel toward the upper and lower edges of the posterior panel, respectively;

wherein the upper and lower portions of the posterior panel have first and second widths such that the first and second widths form the upper and lower edges of the posterior panel and clearances between opposed sides of the main body panel;

wherein the upper and lower portions of the posterior panel space an entirety of the opposed sides of the main body panel from one another.

13. The knee brace of claim 12, wherein the main body panel is untensioned relative to the posterior panel when the posterior panel is secured to the main body panel.

14. A knee brace, comprising:

a main body panel, the main body panel having a first and a second affixation point arranged in a center portion of first and second longitudinal edges of the main body panel;

a posterior panel having a first and a second affixation point arranged in a center portion of first and second longitudinal edges of the posterior panel, respectively, the posterior panel secured to the main body panel at the corresponding first and second affixation points of the main body panel and along a longitudinal length of the main body panel, the main body panel and the posterior panel together forming an elongate, tubular body adapted to anatomically conform to a thigh, knee and calf, with the main body panel generally forming a curved or arcuate cross-section;

first and second hinges located on lateral and medial sides of the knee brace, respectively, the first and second hinges each having upper and lower struts extending from opposed sides of a hinge mechanism, the main body panel including first and second hinge pockets on each of the lateral and medial sides, each hinge mechanism being retained by the main body panel by the first and second hinge pockets;

at least one strap removably mounted on an outer surface of one of the first and second hinge pockets and passes through a strap loop located on the one of the first and second hinge pockets, the at least one strap arranged for extending circumferentially about the knee brace and arranged for being reversed in circumferential orientation in either a laterally-to-medially or medially-to-laterally orientation; and the knee brace further comprising at least one of anterior or posterior straps extending only about an anterior or posterior side of the knee brace, respectively, the at least one of anterior or posterior straps securing to first and second buckles located on the lateral and medial sides, respectively, of the knee brace;

wherein, unworn, the posterior panel forms a posterior contour having a curved configuration such that the first and second affixation points of the posterior panel and main body panel form a point of inflection for the posterior contour located about a central knee portion of the brace;

wherein the knee brace also defines an upper inclined edge sloping downwardly from an anterior aspect of the knee brace to a posterior aspect of the knee brace;

wherein the posterior panel is sized shorter than the main body panel when in an untensioned configuration; and wherein the first and second longitudinal edges of the main body panel respectively secure along the first and second longitudinal edges of the posterior panel when the posterior panel is tensioned by increasing in length from the untensioned configuration;

wherein the first and second longitudinal edges of the main body panel and the posterior panel when tensioned from the shorter, untensioned configuration form first and second longitudinal seams that are posterior to the first and second hinge pockets.

15. The knee brace of claim 14, wherein the at least one of anterior or posterior straps comprises both an anterior strap and a posterior strap.

\* \* \* \* \*